United States Patent [19]

Richardson

[11] 3,960,958

[45] June 1, 1976

[54] 3,4- AND 3,5-DIALKOXYBENZYLAMINES

[75] Inventor: Kenneth Richardson, Canterbury, England

[73] Assignee: Pfizer Inc., New York, N.Y.

[22] Filed: Aug. 26, 1974

[21] Appl. No.: 500,377

[52] U.S. Cl.............................. 260/570.9; 260/404; 260/463; 260/471 C; 260/501.17; 260/501.19; 260/567.5; 260/570.7; 260/570.8 R; 260/606; 424/316; 424/330
[51] Int. Cl.² ........................................ C07C 87/29
[58] Field of Search............ 260/570.9, 404, 501.17, 260/501.19, 567.5

[56] References Cited
UNITED STATES PATENTS 3,419,390 12/1968 Cressman et al.......... 260/570.9 UX

OTHER PUBLICATIONS

Kuehne et al., "Chemical Abstracts," vol. 54, pp. 5502–5505, (1960).

*Primary Examiner*—Robert V. Hines
*Attorney, Agent, or Firm*—Connolly and Hutz

[57] ABSTRACT

Novel benzyl- and phenylethylamines useful as antiviral agents are claimed as well as a process and a pharmaceutical composition for combating viral infections.

9 Claims, No Drawings

3,4- AND 3,5-DIALKOXYBENZYLAMINES

BACKGROUND OF THE INVENTION

This invention relates to novel benzyl- and phenylethylamines useful in combating viral infections in vertebrate animals. It further relates to a novel process for combating viral infection and a novel pharmaceutical composition, both employing said novel amines.

The cells that vertebrates produce, in response to virus infection, a substance which enables cells to resist the multiplication to a variety of viruses. The viral-resisting or viral-interfering substances are referred to as "interferons." They are a heterogeneous group of antiviral proteins which vary quite widely in their molecular weights. Although such proteins may differ in their physico-chemical properties, they all exhibit the same biological properties; namely, they inhibit a wide range of unrelated viruses, have no toxic or other deleterious effects on cells, and are species-specific (Lockart, Frontiers of Biology, Vol. 2, "Interferons," edited by Finter, W. B. Saunder Company, Philadelphia, 1966, pp. 19–20).

This discovery, by Isaacs and Lindenmann, in 1957 (Proc. Roy. Soc. B. 147, 258–267) gave rise to great optimism that an economic preparation of exogeneous interferon might be developed for routine clinical use against viral infections, However, despite great expenditures of effort and money, no safe, effective, economical source has yet been developed. An alternate approach to producing interferon has, therefore, been pursued. This approach comprises administering to the animal to be protected, or treated, a nonviral substance which stimulates—or induces—production of interferon in the cells. The interferon produced in this fashion is referred to as "endogenous" interferon.

The discovery of antiviral compounds is far more complicated and difficult than is the discovery of antibacterial and antifungal agents. This is due, in part, to the close structural similarity of viruses and the structures of certain essential cellular components such as ribonucleic and deoxyribonucleic acids, and to the difficulty of establishing suitable tests for evaluating antiviral agents. However, despite these difficulties, numerous non-viral substances have been found capable of stimulating or inducing interferon formation in animals. Included among such substances are bacteria, parasites, bacterial endotoxins, pyran copolymers, helenine, phytohemagglutinin, polyacrylic compounds, nucleic acids and polynucleotides. Use of these inducers is, however, objected to for one or more reasons, e.g., toxicity, antigenicity, infectiousness, and their routine clinical use appears remote (Zhdanoz et al., Internat'l. Virol I, 1st Int. Congr. Virol, Helsinki 1968, S. Karger, New York, pp. 100-1, 1969).

More recently 2,7-bis[2-(diethylamino)ethoxy]fluorene-9-one dihydrochloride, a purely synthetic material of relatively low molecular weight, has been reported to be an oral inducer of interferon in mice (Abstracts Federation Proceedings, Vol. 29, No. 2, page 635, 1970; Abstracts 2189 and 2190).

A variety of "antiviral agents" are described in the literature. These have been summarized by Osdene in "Topics in Medicinal Chemistry,", edited by Rabinowitz and Myerson, Interscience Publishers, New York, 1968, pages 141–171. For the purposes of his review, Osdene has made use of Herrmann's definition of "antiviral agent" (Herrmann et al., Proc. Soc. Exptl. Biol. Med. 103, 625, 1960); namely, an agent "which can produce either a protective or therapeutic effect to the clear detectable advantage of the virus infected host, or any material that can significantly enhance antibody formation, improve antibody activity, improve non-specific resistance, speed convalescence or depress symptoms." This definition is of such breadth as to cover both prophylactic and therapeutic agents. It includes substances such as interferon, and a host of synthetic materials, such as 1-adamantanamine, pyrimidines, biguanides, guanidine, pteridines to mention a few. It is noted that such synthetic materials are antiviral agents. They are not interferon inducers but operate by a totally different mechanism. Inteferon inducers may, of course, be referred to as antiviral agents. The converse, however, is not true.

Virus infections which attack animals, including man, are normally contagious afflictions which may spread so rapidly that they can reach explosive epidemic proportions in relatively short periods of time. In the past, many of these epidemics have resulted in large numbers of deaths and have been responsible for hugh economic losses. Obviously a method of reducing the incidence of these viral infections, such as the method of this invention, would be welcome as an addition to the armamentarium of medical technology.

SUMMARY OF THE INVENTION

It has now been found that certain novel benzyl- and phenylethylamines are capable of combating viral infections in vertebrate animals susceptible to such infection. The compounds of this invention have the formulae:

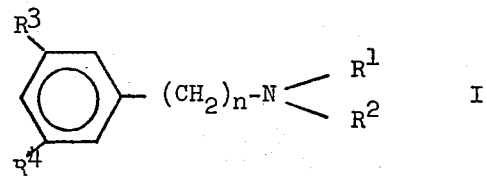

and

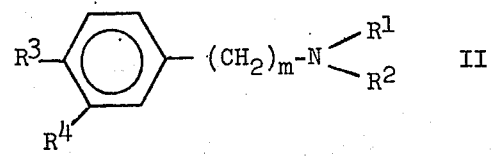

and the pharmaceutically acceptable acid addition salts thereof, wherein $R^1$ is H, methyl or hydroxyalkyl of from 2 to 6 carbon atoms, $R^2$ is H, alkyl of from 1–6 carbon atoms, or hydroxyalkyl of from 2 to 6 carbon atoms, $R^3$ and $R^4$ are each alkoxy of from 12 to 20 carbon atoms, and $m$ and $n$ are each 1 or 2, provided that when $m$ is 1, one of $R_1$ and $R_2$ is hydroxyalkyl of from 2 to 6 carbon atoms and the other is hydrogen.

Also a part of the present invention is a composition in dosage unit form for combating viral infections in vertebrate animals, said composition containing a pharmaceutical diluent and from about 6.0 to 1200 mg. of a compound of formula I or II above as the essential active ingredient.

Especially preferred novel compounds are those in which:

$R^1$ is hydrogen, $R^2$ is ethyl, $R^3$ and $R^4$ are each octadecyloxy, and n is 1;

$R^1$ is hydrogen, $R^2$ is ethyl, $R^3$ and $R^4$ are each eicosyloxy, and n is 1; and $R^1$ is hydrogen, $R^2$ is hydroxyethyl, $R^3$ and $R^4$ are each octadecyloxy, and m is 1.

By pharmaceutically acceptable acid addition salts is meant those salts which are non-toxic at the dosages administered. The acid addition salts of the above-mentioned bases which may be employed are the water-soluble and water-insoluble salts such as the hydrochloride, hydrobromide, phosphate, nitrate, sulfate, acetate, mesylate, hexafluorophosphate, citrate, gluconate, benzoate, propionate, butyrate, sulfosalicylate, maleate, laurate, malate, fumarate, succinate, oxalate, tartrate, amsonate, (4,4'-diaminostilbene-2,2'-disulfonate), pamoate (1,1'-methylene-bis-2-hydroxy-3-naphthoate, stearate, 3-hydroxy-2-naphthoate, p-toluenesulfonate, picrate, lactate and suramin salt.

In the compounds of Formula I, $R^3$ and $R^4$ are meta to each other and in the compounds of Formuls II, they are ortho to each other.

A further aspect of the present invention is a process for combating viral infections in vertebrate animals which comprises administering to a subject susceptible to such infection a composition containing an effective amount of a compound of formulae I and/or II as the essential active ingredient. By combating is meant both the prophylactic treatment and the actual therapeutic treatment of infected subjects.

DETAILED DESCRIPTION OF THE INVENTION

The compounds described herein exhibit broad spectrum activity against a variety of viruses in vivo when adminstered parenterally (subcutaneously, intramuscularly, intraperitoneally), intranasally (e.g. by inhalation or spray), or topically to vertebrate animals. This usefulness is primarily one of prophylactic rather than of therapeutic control of virus infections. Although the present invention is not to be construed as limited by such a theory, it is possible that the compounds of this invention function in combating viral infections by virtue of their ability to induce the production of endogenous interferon. They induce interferon in vivo, but they cannot do so directly in cell cultures. They, therefore, can be considered as stimulators of host defense mechanisms.

Further, these compounds stimulate the animal body to produce interferon when administered alone or in combination with an otherwise inactive substance, for example, single-stranded ribonucleic acid, such as highly polymerized ribonucleic acid from yeast, yeast nucleic acid (Calbiochem 55712, Calbiochem, Los Angeles, California). Those compounds which induce interferon when administered alone are given at considerably lower doses when given in combination with the single-stranded ribonucleic acid or other such material.

The compounds of formula II are conveniently prepared by the following novel routes of synthesis:

In one synthesis, 3,4-dihydroxybenzaldehyde is employed as a starting material. It is reacted with two moles of an alkyl halide, preferably an alkyl bromide in the presence of a base such as potassium carbonate. The reaction is conducted in the presence of an inert organic solvent such as acetone.

The 3,4-dialkoxybenzaldehyde thus formed is further reacted with ethanolamine in the form of a salt, such as a hydrochloride, in the presence of sodium or lithium cyanoborohydride to form an N-(2-ethanol)-3,4-dialkoxybenzylamine salt. The compound may be purified by standard means such as chromatography.

In a second synthesis, the compounds of formula II are prepared using 3,4-dihydroxy phenylethylamine as a starting material. This compound is reacted with benzylchloroformate and this derivative is reacted with two moles of an alkyl halide in the presence of a base such as potassium carbonate.

This 3,4-dialkoxy derivative is then hydrogenolysed to provide the 3,4-dialkoxyphenethylamine.

The compounds of formula I are prepared by the following novel synthetic routes.

One synthesis employs 3,5-dihydroxybenzamide as a starting material. This compound is reacted with an alkyl halide, preferably an alkyl bromide, in the presence of a base such as potassium carbonate and an inert organic solvent such as ethanol. The product is a 3,5-dialkoxy benzamide. This product is reduced using any of a wide variety of reducing agents such as aluminum hydride, lithium aluminum hydride or preferably Na-bis-2-(methoxyethyoxy) aluminum hydride (70% solution in benzene) to form a 3,5-dialkoxy benzylamine which is then purified by standard means.

Another synthesis of the ompounds of formula I employs the same starting material and also uses an alkyl halide to form the 3,5-dialkoxy benzamide followed by reduction to the corresponding benzylamine. Then the 3,5-dialkoxy benzylamine is reacted with a carbonyl halide, preferably a carbonyl chloride, to form a N-carbonyl-3,5-dialkoxy benzylamine. This is then reduced by reducing agents such as aluminum hydride or Na-bis-2-(methoxyethoxy)aluminum hydride (70% solution in benzene) to form a N-alkyl-3,5-dialkoxy benzylamine which may be purified by standard means.

Acid addition salts of the compounds described herein are prepared by conventional procedures as by mixing the amine compound in a suitable solvent with the required acid and recovering the salt by evaporation or by precipitation by addition of a non-solvent for the salt. Hydrochloride salts are readily prepared by passing dry hydrogen chloride through a solution of the amine compound in an organic solvent such as ether.

The antiviral activity of the above-described materials is determined by the following procedure. The test compound is administered to mice by the intraperitoneal route eighteen to twenty-four hours prior to challenging the mice with a lethal dose of encephalomyocarditis virus and determining the survival rate ten days after challenge. The procedure in which the drug is given eighteen to twenty-four hours before and at a distinctly different site from virus injection is designed to eliminate local effects between drug and virus and select only compounds which produce a systemic interferon response.

The test compounds are administered alone and in combination with from about 2 to about 20 times by weight of an otherwise inactive (non-inducer of interferon and nonantiviral), single-stranded, highly polymerized ribonucleic acid from yeast, yeast nucleic acid.

Table I below gives the results of such tests on mice.

When administered parenterally, the materials of this invention are used at a level of from about 0.1 mg/kg of body weight to about 20 mg/kg of body weight. The favored range is from about 0.1 mg/kg to about 5.0 mg/kg of body weight. The dosage, of course, is dependent upon the animal being treated and the particular amine compound involved and is to be determined by the individual responsible for its administration. Generally, small doses will be administered initially with gradual increase in dosage until the optimal dosage level is determined for the particular subject under treatment.

Intramuscular injections are the preferred method of parenteral injection for several reasons such as simplicity and convenience. Vehicles suitable for parenteral injection may be either aqueous such as water, isotonic saline, isotonic dextrose, Ringer's solution, or non-aqueous such as fatty oils of vegetable origin (cottonseed, peanut oil, corn, sesame) and other non-aqueous vehicles which will not interfere with the efficacy of the preparation and are nontoxic in the volume or proportion used (glycerol, ethanol, propylene glycol, sorbi-

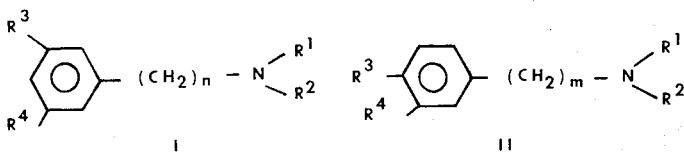

| Compound | Dose (Mg/bg body weight) | % Survivors |
|---|---|---|
| 1. Formula II | | |
| $R^1$ and $R^2$ are each | 15 | 50 |
| hydrogen, $R^3$ and $R^4$ are | 5 | 30 |
| each octadecyloxy, and m is 2 | 1.5 | 40 |
| 2. Formula I | | |
| $R^1$ and $R^2$ are each hydrogen, | 15 | 70 |
| $R^3$ and $R^4$ are each hexadecyloxy, | 5 | 50 |
| and n is 1. | 1.5 | 0 |
| 3. Formula I | | |
| $R^1$ is hydrogen, $R^2$ is ethyl, | 15 | 70 |
| $R^3$ and $R^4$ are each hexadecyloxy, | 5 | 60 |
| and n is 1. | 1.5 | 50 |
| 4. Formula I | | |
| $R^1$ and $R^2$ are each hydrogen, | 15 | 80 |
| $R^3$ and $R^4$ are each octadecyloxy, | 5 | 10 |
| and n is 1. | 1.5 | 10 |
| 5. Formula I | 50 | 70 |
| $R^1$ is hydrogen, $R^2$ is ethyl, | 15 | 50 |
| $R^3$ and $R^4$ is octadecyloxy, and | 5 | 40 |
| n is 1. | 1.5 | 0 |
| 6. Formula II | 50 | 70 |
| $R^1$ is hydroxyethyl, $R^2$ is | 15 | 60 |
| hydrogen, $R^3$ and $R^4$ are each | 5 | 30 |
| hexadecyloxy, and m is 1. | 1.5 | 10 |

Parenteral, topical and intranasal administration of the above-described amines to an animal, including man, before exposure of the animal to an infectious virus provide rapid resistance to the virus. The resistance engendered is non-specific and is effective against a great number of viruses. Such administration is effective when given as much as five days prior to exposure to the virus. Preferably, however, administration should take place from about three days to about one day before exposure to the virus, although this will vary somewhat with the particular animal species and the particular infectious virus. The compounds of the present invention may be employed effectively in a range of from 0.1 to 20 mg/kg body weight on a daily basis and a preferred range is from 0.1 to 5.0 mg/kg body weight.

tol). Additionally, compositions suitable for extemporaneous preparation of solutions prior to administration may advantageously be made. Such compositions may include liquid diluents, for example, propylene glycol, diethyl carbonate, glycerol, sorbitol.

When the materials of this invention are administered, they are most easily and economically used in a dispersed form in an acceptable carrier. When it is said that this material is dispersed, it means that the particles may be molecular in size and held in true solution in a suitable solvent or that the particles may be colloidal in size and dispersed through a liquid phase in the form of a suspension or an emulsion. The term "dispersed" also means that the particles may be mixed with and spread throughout a solid carrier so that the mixture is in the form of a powder or dust. This term is also meant to encompass mixtures which are suitable for use as sprays, including solutions, suspensions or emulsions of the agents of this invention.

In practicing the intranasal route of administration of this invention any practical method can be used to contact the inducer with the respiratory tract of the animal. Effective methods include administration of the inducer by intranasal or nasopharyngeal drops and by inhalation as delivered by a nebulizer or an aerosol. Such methods of administration are of practical importance because they provide an easy, safe and efficient method of practicing this invention. For intranasal administration of the inducer, usually in an acceptable carrier, a concentration of inducer between 0.1 mg/ml and 20 mg/ml is satisfactory and convenient.

For topical application the inducers are most conveniently used in an acceptable carrier to permit ease and control of application and better absorption. Here also concentrations in the range of from about 0.1 mg/ml to about 20 mg/ml are satisfactory. In general, in the above two methods of administration a dose within the range of about 0.1 mg/kg to about 20 mg/kg of body weight and, preferably, from about 0.1 mg/kg to about 5.0 mg/kg of body weight will be administered.

The compounds employed in this invention may be employed alone, i.e., without other medicinals, as mixtures of more than one of the herein-described compounds or in combination with other medicinal agents, such as analgesics, anesthetics, antiseptics, decongestants, antibiotics, vaccines, buffering agents and inorganic salts, to afford desirable pharmacological properties. Further, they may be administered in combination with hyaluronidase to avoid or, at least, to minimize local irritation and to increase the rate of absorption of the compound. Hyaluronidase levels of at least about 150 (U.S.P.) units are effective in this respect although higher or lower levels can, of course, be used.

Those materials of this invention which are water-insoluble, including those which are of low and/or difficult solubility in water, are, for optimum results, administered in formulations, e.g., suspensions, emulsions, which permit formation of particle sizes of less than about $20\mu$. The particle sizes of the formulations influence their biological activity apparently through better adsorption of the active materials. In formulating these materials various surface active agents are the partial esters of common fatty acids, such as lauric, oleic, stearic, with hexitol anhydrides derived from sorbitol, and the polyoxyethylene derivatives of such ester products. Such products are sold under the trademarks "Spans" and "Tweens," respectively, and are available from the Atlas Powder Co., Wilmington, Delaware. Cellulose ethers, especially cellulose methyl ether (Methocel, available from the Dow Chemcial Co., Midland, Michigan) are highly efficient as protective colloids for use in emulsions containing the materials of this invention.

In some cases, the compositions of the present invention are desirably administered by aerosol spray. For such application, a halogenated hydrocarbon propellant of up to 2 carbon atoms is employed. The propellant may be any of the conventional propellants used in aerosol formulations, for example halogenated hydrocarbons of the fluorohydrocarbon or fluorohalohydrocarbon type such as trichloromonofluoromethane, dichlorodifluoromethane, dichlortetrafluoroethane, monochlorotrifluoromethane, monochlorodifluoromethane and mixtures of any of these together or with other propellants. Typical of suitable propellants are those disclosed in, for example, U.S. Pat. No. 2,868,691 and sold under the trademark Freon.

The examples to follow are illustrative and in no way limit the scope of the appended claims.

EXAMPLE I 3,4(Dihexadecyloxy)Benzaldehyde 20.7 g. (0.15 m) 3,4-Dihydroxylbenzaldehyde, (Aldrich), 91.5 g. (0.30 m) - Hexadecyl Bromide (Humphrey Chem), and 41.1 g (0.30 m) Potassium Carbonate were combined in 750 ml acetone, and refluxed overnight. The material was filtered hot and washed well with acetone. A precipitate formed upon cooling. This was filtered, washed with acetone and air dried to a white solid (38.3 g).

N-2-Hydroxyethyl-3,4-(dihexadecyloxy)benzylamine HCl 3,4-(Dihexadecyloxy)benzaldehyde (4.40 g), sodium cyanoborohydride (0.284 g), methanol (20 ml) and tetrahydrofuran (80 ml) were combined and the pH adjusted to 5.0 with 5N methanolic HCl. The mixture was stirred at room temperature, and when the reaction was complete (9 days), the pH was adjusted to 2.0 with concentrated HCl, and the solvent was removed on a rotary evaporator. The resulting material was treated with $CHCl_3/H_2O$ (1/1; 100 ml) and 10% NaOH (adjusted pH of solution to 10.0). The aqueous phase was separated and extracted with $CHCl_3$ (3 × 50), and the combined organic extracts were washed with $H_2O$ (50 ml) and a solution of saturated NaCl (2 × 50) and dried over $Na_2SO_4$. This mixture was filtered and the resulting solution evaporated to give the crude product. Column chromatography on silica gel eluting with $CHCl_3$ and ethyl acetate provided pure N-2-hydroxyethyl-3,4-(dihexadecyloxy)benzylamine. The HCl salt was prepared by standard methods (m.p. 190°–192°).

EXAMPLE II

Part A - 3,5-(dioctadecyloxy)benzamide 7.65 g (0.05 m) of 3,5-dihydroxybenzamide (Aldrich), 33.3 g. (0.1 m) 1-bromooctadecane, and 13.8 g (0.1 m) potassium carbonate were slurried in 100 ml ethanol and refluxed overnight. The reaction was cooled to room temperature, and the solid was extracted with benzene. The extracts were dried over sodium sulfate, filtered and evaporated in vacuo to a yellowish solid. This was recrystallized from ethanol to yield 24.7 g of a white solid, m.p. 100°–102.5°C.

Part B - 3,5-(dioctadecyloxy)benzylamine 20 g (0.03 m) of the product above was slurried in 200 ml benzene and 54 ml Na-bis(2-methoxyethoxy)aluminum hydride (70% solution in benzene) was added. A clear greenish-yellow solution resulted which when refluxed for 7 hours gradually turned deep red. The solution was allowed to stand at room temperature overnight and it became cloudy while 50 ml of 10% NaOH was added dropwise and the mixture was treated with water and benzene. The benzene extracts were dried over sodium sulfate and evaporated in vacuo to a white solid (22.3 g). This was dissolved in chloroform and HCl was bubbled in for 10 minutes. It was again evaporated in vacuo and dried to yield 13.6 g of a white solid, m.p. 82.5°–85°C.

The following compound was prepared in a similar manner.

| Compound | Melting Point °C. | Description |
|---|---|---|
| C. 3,5-(dihexadecyloxy) benzylamine | 73–74.5 | white solid (HCl) |

EXAMPLE III

N-acetyl-3,5-(dioctadecyloxy)benzylamine

The product of Example II, Part B (3.4 g, 0.005 m) was slurried in 80 ml methylene dichloride. Then 1.26 g (0.0125) m) was added followed by 0.98 g (0.0125 m) acetyl chloride in 10 ml methylene dichloride. The resulting clear solution was stirred at room temperature overnight and a fine precipitate formed. The reaction was washed with water (3 × 100 ml) and the methylene dichloride phase was dried over sodium sulfate, filtered, and concentrated in vacuo to a white semi-solid. This was slurried in acetone, filtered, and dried to yield a white solid (2.4 g, m.p. 77°–78°C.).

3,5-(dioctadecyloxy)-N-ethyl-benzylamine HCl 2.0 g (0.0029 m) N-acetyl-3,5-(dioctadecyloxy)-benzylamine was slurried in 65 ml benzene. The 5.16 ml sodium-bis-2-methoxyethoxy-aluminum hydride (70% solution in benzene, Aldrich) was added. The resulting clear solution was heated to reflux for 5 hours and then held at room temperature overnight. The reaction was cooled to 15°C. for 20 ml 10% NaOH as added dropwise. The benzene phase formed was washed 2 × 20 ml 10% NaOH and dried over sodium sulfate, filtered, and concentrated in vacuo to 1.99 g of a viscous oil. This was chromatographed on silica gel and eluted with ethyl acetate to yield 1.06 g of product. This was dissolved in cloroform, and 10 ml ethyl acetate/HCl was added. The resulting solution was concentrated in vacuo to a white solid (0.960 g, m.p. 97°–101°C.).

By the same procedures the following compound was made.

| Compound | Melting Point (°C.) | Description |
|---|---|---|
| 3,5-(dihexadecyloxy)-N-ethylbenzylamine HCl | 99–102 | white solid (HCl) |

EXAMPLE IV

Part A - N-Benzyloxycarbony(3,4-Dihydroxyphenethylamine)

3-Hydroxytyramine hydrochloride (8.05 g 0.0425 mole) dissolved in N,N-Dimethylformamide (25 ml) was purged with nitrogen and then treated with triethylamine (6 ml). After stirring for 15 mins., carbobenzyloxy chloride (3.6 g) and triethylamine (3 ml) were added and the reaction was stirred for 15 minutes. Further portions of carbobenzyloxy chloride (3.6 g) and triethylamine (3 ml) were added and the reaction mixture was stirred at room temperature for 1 hour. Ether (500 ml) and water (125 ml) were added and the ether layer was washed with water (125 ml) and dried (Na$_2$SO$_4$) and then evaporated. The residual oil was dissolved in boiling benzene (150 ml) and then cooled to room temperature. The white crystals were collected and dried to yield the product 4.69 g m.p. 129°–130°C. (J. Med. Chem., (1973) 16, p. 630 m.p. 128°).

Part B - N-Benzyloxycarbonyl(3,4-Dioctadecyloxyphenethylamine)

The product from Part A (2.87 g) was dissolved in ethanol (50 ml) and treated with octadecyl bromide (6.66 g) and potassium carbonate (2.76 g). This mixture was refluxed and stirred 18 hours and then cooled and treated with benzene (500 ml) and water (300 ml) and a small amount of ethyl acetate to aid separation. The organic layer was washed with water, dried (Na$_2$SO$_4$), and evaporated. The resulting solid was dissolved in chloroform and chromatographed on silica with chloroform elution. The first fractions were evaporated to yield the product, 5.39 g, m.p. 72°–73° (structure confirmed by proton magnetic resonance spectroscopy).

EXAMPLE IV

Part C - 3,4-Diotadecyloxyphenethylamine hydrochloride

The product from Part B (2.96 g 0.00375 mole) and 10% palladium on charcoal (1.58 g) and benzene (200 ml) were mixed and shaken on a Parr Shaker with hydrogen at an initial pressure of 59 lbs./sq. in. Shaken 1½ hours, and pressure dropped to 56 lbs., filtered and filtrate evaporated to yield a white semi-solid. This was dissolved in chloroform, saturated with hydrogen chloride gas and evaporated to yield the product. 2.31 g (89%) m.p. 75°–77° (structure confirmed by proton magnetic resonance spectroscopy).

EXAMPLE V

| Nasal Spray or Nasal Solution | | mg/ml |
|---|---|---|
| 3,5-dihexadecyloxy-benzylamine HCl | | 51.0 |
| Polysorbate 80 | USP | 50.0 |
| Glycerin | USP | 50.0 |
| Phenyl Ethyl Alcohol | NF | 2.5 |
| Sodium Metabisulfite | USP | 1.0 |
| Sodium Phosphate Monobasic Hydrous | | 1.4 |
| Sodium Hydroxide | USP | 0.2 |
| Sodium Chloride | USP | 7.9 |
| Water for Injection | USP | 842.0 |
| | | 1006.0 |

The resulting solution is packaged into a suitable plastic nebulizer or a suitable dropper bottle.

EXAMPLE VI

Injectable Dosage Form 3,5-(Dioctadecyloxy)benzylamine in powder form is used in filling ampules, each ampule containing 1 mg. Each ampule is flushed with nitrogen and sealed. Before use the ampule is filled with 0.9% saline solution for injection.

What is claimed is:

1. A compound selected from those of the formulae:

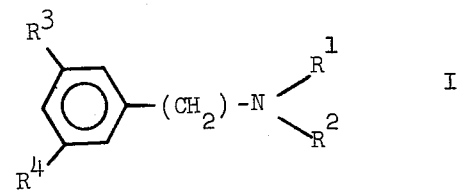

and

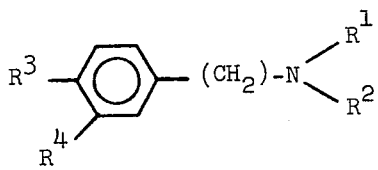  II and the pharmaceutically acceptable acid addition salts thereof, wherein R¹ is H, methyl or hydroxyalkyl of from 2 to 6 carbon atoms;

R² is H, alkyl of from 1 to 6 carbon atoms, or hydroxyalkyl from 2 to 6 carbon atoms, and R³ and R⁴ are each alkoxy of from 12 to 20 carbon atoms, provided that when R³ is ortho to R⁴, one of R¹ and R² is hydroxyalkyl of from 2 to 6 carbon atoms and the other is hydrogen.

2. A compound according to claim 1 wherein R¹ is hydrogen, R² is ethyl, and R³ and R⁴ are each octadecyloxy and meta to each other.

3. A compound according to claim 1 wherein R¹ is hydrogen, R² is ethyl, and R³ and R⁴ are each eicosyloxy and meta to each other.

4. A compound according to claim 1 wherein R¹ is hydrogen, R² is hydroxyethyl, and R³ and R⁴ are each octadecyloxy and ortho to each other.

5. A compound according to claim 1 wherein R¹ is hydrogen.

6. A compound according to claim 1 wherein R³ and R⁴ are meta to each other.

7. A compound according to claim 1 wherein R³ and R⁴ are ortho to each other.

8. A compound according to claim 1 wherein R³ and R⁴ are the same.

9. A compound according to claim 1 wherein R¹ and R² are hydrogen, and R³ and R⁴ are octadecyloxy and meta to each other.

* * * * *